(12) United States Patent
Kück et al.

(10) Patent No.: US 10,801,965 B2
(45) Date of Patent: Oct. 13, 2020

(54) GAS MEASUREMENT SYSTEM

(71) Applicant: DRÄGER SAFETY AG & CO. KGaA, Lübeck (DE)

(72) Inventors: Kal Kück, Hamburg (DE);
Hans-Ullrich Hansmann, Barnitz (DE); Detlef Ott, Lübeck (DE);
Andreas Mohrmann, Krummesse (DE); Arne Tröllsch, Lübeck (DE)

(73) Assignee: DRÄGER SAFETY AG & CO. KGaA, Lübeck (DE)

( * ) Notice: Subject to any disclaimer, the term of this patent is extended or adjusted under 35 U.S.C. 154(b) by 1136 days.

(21) Appl. No.: 14/415,355

(22) PCT Filed: Jul. 17, 2013

(86) PCT No.: PCT/EP2013/065091
§ 371 (c)(1),
(2) Date: Jan. 16, 2015

(87) PCT Pub. No.: WO2014/012974
PCT Pub. Date: Jan. 23, 2014

(65) Prior Publication Data
US 2015/0168307 A1    Jun. 18, 2015

(30) Foreign Application Priority Data
Jul. 20, 2012 (DE) .................. 10 2012 014 503

(51) Int. Cl.
*G01N 21/78* (2006.01)
*G01N 21/05* (2006.01)
(Continued)

(52) U.S. Cl.
CPC .......... *G01N 21/783* (2013.01); *G01N 21/05* (2013.01); *G01N 21/8483* (2013.01);
(Continued)

(58) Field of Classification Search
CPC .. G01N 21/783; G01N 21/05; G01N 21/8483; G01N 33/0027; G01N 2201/062; Y10T 436/202499
See application file for complete search history.

(56) References Cited

U.S. PATENT DOCUMENTS

| | | |
|---|---|---|
| 2,232,622 A | 2/1941 | Moses et al. |
| 2,551,281 A | 5/1951 | Moses et al. |

(Continued)

FOREIGN PATENT DOCUMENTS

| | | |
|---|---|---|
| CN | 16 03 797 A | 4/2005 |
| CN | 18 82 832 A | 12/2006 |

(Continued)

OTHER PUBLICATIONS

Fujitsuka, Norio, et al. "Monolithic pyroelectric infrared image sensor using PVDF thin film." Sensors and Actuators A: Physical 66.1-3 (1998): 237-243.*

(Continued)

*Primary Examiner* — Robert J Eom
(74) *Attorney, Agent, or Firm* — McGlew and Tuttle, P.C.

(57) ABSTRACT

A gas measurement system for measuring the concentration of gaseous and/or vaporous components of a gas mixture by means of the color change of at least one reaction substance on a reaction support unit in which the at least one reaction substance is arranged on the reaction support unit separately within at least two light permeable channels is provided in such a manner that data can be read out reliably at low technical expense. The data reading device can be designed as a digital camera and/or as a reading apparatus for an electronic data storage device.

37 Claims, 7 Drawing Sheets

(51) Int. Cl.
*G01N 21/84* (2006.01)
*G01N 33/00* (2006.01)

(52) U.S. Cl.
CPC ... *G01N 33/0027* (2013.01); *G01N 2201/062* (2013.01); *Y10T 436/202499* (2015.01)

(56) References Cited

U.S. PATENT DOCUMENTS

| | | |
|---|---|---|
| 5,089,232 A | 2/1992 | May |
| 5,397,538 A | 3/1995 | Stark et al. |
| 6,422,061 B1 * | 7/2002 | Sunshine ............. G01N 29/022 340/603 |
| 2005/0083527 A1 | 4/2005 | Flaherty et al. |
| 2005/0196322 A1 | 9/2005 | Truex et al. |
| 2008/0237040 A1 | 10/2008 | Wessel |
| 2009/0223287 A1 | 9/2009 | Dai et al. |
| 2010/0015006 A1 | 1/2010 | Hsu |

FOREIGN PATENT DOCUMENTS

| | | |
|---|---|---|
| CN | 101 275 925 A | 10/2008 |
| CN | 101 548 183 A | 9/2009 |
| CN | 101 936 912 A | 1/2011 |
| CN | 101 949 857 A | 1/2011 |
| CN | 101 990 635 A | 3/2011 |
| CN | 102216782 A | 10/2011 |
| CN | 102 565 040 A | 7/2012 |
| DE | 39 02 402 C1 | 6/1990 |
| DE | 43 03 858 C2 | 8/1995 |
| DE | 10 2009 048 915 A1 | 4/2011 |
| EP | 1 974 817 A2 | 10/2008 |
| WO | 2008/119039 A2 | 10/2008 |

OTHER PUBLICATIONS

Definition "Digital Camera"; https://www.dictionary.com/browse/digital-camera; (accessed Jan. 22, 2020) ; p. 1-4.*
English translation of Chinese Search Report dated May 17, 2016.

* cited by examiner

GAS MEASUREMENT SYSTEM

TECHNICAL FIELD

The current subject matter is directed to a gas measurement system in which data can be transmitted to and/or received from a reaction support unit on which reaction substances are disposed.

BACKGROUND

Gas measurement systems are used for measuring the concentration of gaseous and/or vaporous components of a gas mixture by means of a color change of at least one reaction substance. On a reaction support unit with a chip or a plate, transparent glass tubes are arranged on the chip. The same or a different reaction substance is arranged within the glass tube. A remaining gas measurement system comprises a suction pump for conveying the gas mixture through the glass tube and thus to the reaction substance as well as a mechanical bearing in the form of friction bearing for the reaction support unit. Here, the reaction support unit is introduced first as an exchangeable unit into the remaining gas measurement system, and then the reaction support unit is moved by a servomotor into a predetermined position. Through a gas connector, the gas mixture is conveyed through the gas tube by the suction pump, and in the case of the presence of gaseous and/or vaporous components on which the reaction substance produces a color change, a color change of the reaction substance occurs. This color change is detected by an optoelectronic detection device, namely a number, for example, 6 Si diodes, and the data acquired by an optoelectronic detection unit are evaluated by an evaluating device. For this purpose, on the reaction support unit, on a barcode, data are stored in bar code form as a means for storing information, read by the Si diodes, and transferred to the evaluating device. These data are required for the evaluation, for example, data pertaining to the type of the reaction substance. Disadvantageously, only a small amount of data can be stored in bar code form on the barcode, and the readout is prone to malfunction. Such gas measurement systems are used, for example, at work sites, in special waste dumps, or in the case of accidents involving chemicals, in order to be able to rapidly detect outflowing noxious substances of unknown type and concentration.

DE 39 02 402 C1 shows a device for measuring the concentration of gaseous and/or vaporous components of a gas mixture using optically detectable reaction zones of gas test tubes containing a substance that reacts with the a component to be detected, wherein the change of the reaction zone can be determined by direct observation and/or by an optoelectronic scanning device. Here, several channels are arranged on a support in chip form that is exchangeable and insertable in an optoelectronic scanning device. The scanning device is designed here as an LED array.

DE 43 03 858 C2 shows a device for the colorimetric detection of gaseous and/or vaporous components of a gas mixture on the basis of a discoloration of a reaction zone arranged in a channel, one or more of which are applied on a transparent support in disk form which can be moved into an evaluation position which is detected by a signal transmission unit in a signal receiving unit. A barcode as data field is also arranged on the support. The signal receiving units here are designed as CCD sensors. For example, they can be silicon photodiodes or silicon transistors.

The problem of the present invention therefore consists in providing a gas measurement system, a reaction support unit, and a method for operating a gas measurement system, in which the data can be read on a means for storing data on the reaction support unit at low technical expense, and larger data quantities can also be stored cost effectively.

SUMMARY

The current subject provides a gas measurement system, a reaction support unit, and a method for operating a gas measurement system, in which the data can be read on a means for storing data on the reaction support unit at low technical expense, and larger data quantities can also be stored cost effectively. In particular, a gas measurement system or a gas measurement arrangement can be provided for measuring the concentration of gaseous and/or vaporous components of a gas mixture by means of a color change of at least one reaction substance on a reaction support unit, wherein the at least one reaction substance is arranged on the reaction support unit separately within at least two light permeable channels, the gas measurement system comprising a gas conveyance device for conveying the gas mixture through a channel and to the at least one reaction substance, a mechanical bearing, in particular a friction bearing, for the reaction support unit, (e.g., a motor, etc.) for moving the reaction support unit or another component, so that the gas mixture can be conveyed separately through one of the at least two channels, an optoelectronic detection device for detecting a color change of the at least one reaction substance during and/or after the conveyance of the gas mixture through a channel, wherein, for example, in the direction of flow of the gas mixture through the channel, the color change can be detected in at least two separate positions, a data reading device for the readout of data stored on the reaction support unit, an evaluating device for evaluating the data acquired by the optoelectronic detection unit, and an optical and/or acoustic display device for displaying the data evaluated by the evaluating unit, wherein the data reading unit is designed as a digital camera and/or as a reading device for an electronic data storage device.

Using the digital camera, a large-area matrix code on the reaction support unit can also be read out advantageously, thus making it also possible to read out with the camera larger data quantities that are stored on the matrix code. The digital camera is here capable of taking a photo of the matrix code, which can be assessed subsequently by the evaluating device on the basis of appropriate software. Using the reading apparatus for electronic data storage devices, it is also possible to read out electronic data storage devices, for example, RFID chips. As a result, for storing data on the reaction support unit, it is advantageously possible to use not only optical systems, such as an optical code, but also electronic data storage devices for the secure storage of larger data quantities.

In an additional variant, the reading apparatus comprises a receiver, for example, an antenna, and a transmitter, for example, an antenna, for wireless signals, for example, alternating magnetic fields or radio waves. RFID chips are read out, for example, by means of alternating magnetic fields or radio waves.

In an additional embodiment, the reading apparatus comprises electrical contact elements for the hard-wired data transfer from the reaction support unit to the gas measurement system, and vice versa. By means of electrical contact elements, an electrical connection can be established between the electronic data storage device and the (remaining) gas measurement system, particularly the reading apparatus and/or the evaluating device, for the data transfer from the electronic data storage device to the gas measurement system, for example, the evaluating device and/or the reading apparatus. The remaining gas measurement system is the gas measurement system without the reaction support unit.

In an additional variant, the reading apparatus comprises a bus system or a portion of a bus system for the hard-wired data transfer from the reaction support unit to the gas measurement system, and vice versa. Like a hard-wired data transfer, the bus system can also transfer not only data but also electrical energy to the electronic data storage device. This allows a particularly reliable data transfer.

In an additional embodiment, the reading apparatus is formed at least partially, in particular entirely, by the evaluating device. It is possible to incorporate appropriate devices, for example, a transmitter or a receiver, in the evaluating device, so that the evaluating device also constitutes the reading apparatus.

In a further embodiment, the digital camera is formed with an electronic image converter or image sensor and with an imaging optics system (e.g., a lens system, etc.) and/or the digital camera is designed as a camera chip, particularly a CMOS camera chip and/or the optoelectronic detection device is formed by the digital camera. The digital camera can thus be used not only for reading out the matrix code, but also as an optoelectronic detection device for detecting the color change of the at least one reaction substance.

The motor can be designed as an electric motor, in particular a servomotor, and the motor can be brought by means of a drive roller into effective mechanical connection with the reaction support unit, and/or the evaluating device comprises a processor, for example, a microcontroller, and an evaluation data storage device, and/or the indicator device comprises a monitor and/or a light emitter, for example, a lamp or an LED, and/or a signal tone generator, and/or, by means of the gas measurement system, a method described in this patent application can be carried out, and/or the gas measurement system comprises the reaction support unit described in this patent application.

A reaction support unit according to a gas measurement system can include a chip and/or a plate, and tubes arranged on the chip or the plate, in particular glass tubes that delimit the channels, and the at least one reaction substance is arranged within the tubes, and a means for storing data, wherein the means for storing data is designed as matrix coding, in particular a matrix barcode, or as an electronic data storage device. The reaction support unit can thus store a large data quantity reliably and consistently cost effectively with matrix coding or the electronic data storage device. In addition, it is also possible to store the data on the electronic data storage device, while the reaction support unit on the remaining gas system is on the remaining gas measurement system or the gas measurement system. This results in new possibilities for the operation of the gas measurement system.

In an additional variant, the electronic data storage device is designed as a RFID chip or as a RAM data storage device, particularly an SRAM chip or an NVRAM chip, or as a ROM data storage device, particularly a PROM chip or an EPROM chip, and/or the reaction support unit comprises a transmitter, for example, an antenna, and a receiver, for example, an antenna, for wireless signals, for example, alternating magnetic fields or radio waves and/or the reaction support unit comprises electrical contact elements and/or a bus system or a portion of a bus system for the hard-wired data transfer from the reaction support unit to the gas measurement system, and vice versa.

In an additional embodiment, the matrix coding is designed as a printed matrix coding, in particular printed on the chip or the plate, and the matrix coding is designed as an LED arrangement. The matrix coding is, for example, a matrix coding printed on the chip or the plate as a black and white print. Such matrix codings cannot be modified, and they can be read out simply by the digital camera. In contrast, the matrix arrangement can also be designed as an LED arrangement. Here, a larger number of LEDs, particularly OLEDs, are arranged in rows and columns, and depending on which of the LEDs is switched on or off, specific information can be stored in this manner. For this purpose, the reaction support unit comprises an energy supply unit, for example, a battery, and a control unit which controls which of the LEDs is switched on or off. As a result, changes of the matrix coding can be produced, including as a function of time, so that as a result different matrix codings can be made available in a simple manner by an identical reaction support unit. In this manner, only corresponding other data need to be transferred to the control unit, so that other LEDs are accordingly switched on or off by said control unit.

A method for operating a gas measurement system, in particular a gas measurement system can include moving a reaction support unit or another component with a motor, transferring data from a means for storing data in the reaction support unit by means of a data reading device to the (remaining) gas measurement system, particularly to an evaluating device of the gas measurement system, conveying a gas mixture through a, particularly only one, channel with at least one reaction substance by means of a gas conveyance device, detecting by means of an optoelectronic detection device a color change of the at least one reaction substance during and/or after the conveyance of the gas mixture through the channel, wherein in the direction of flow of the gas mixture through the channel the color change is detected in at least two separate positions, evaluating the data detected by the optoelectronic detection device with regard to the color change by means of an evaluating device, optical and/or acoustic display of the data evaluated by the evaluating device by means of a display device, wherein the data are read out from a matrix code or an electronic data storage device.

In an additional variant, the data are read out optically with a digital camera or by a hard-wired or wireless process, in particular by means of radio waves or a modifiable magnetic field, with a reading apparatus. During the optical read out of the data by means of the digital camera from the matrix code, a photo of the entire matrix code is produced by the digital camera, and the data of this photo are subsequently transferred to the evaluating device, and evaluated by the latter. As a result, the data that are optically stored in the matrix code can be transferred to the evaluating device. As a radio connection, a Bluetooth radio connection can be used, for example.

In an additional design, data, for example, data pertaining to the concentration of gaseous and/or vaporous components of the gas mixture, are transferred to the electronic data storage device, in particular from the evaluating device, in particular by means of the reading apparatus, and/or the color change of the at least one reaction substance is detected, in particular exclusively with a digital camera. In the electronic data storage device, for example, the RFID chip, data can also be stored. For example, the concentrations of gaseous and/or vaporous components detected with the reaction support unit can be stored in the electronic data storage device after the evaluation of the data with respect to the color changes by means of the evaluating device in the electronic data storage device. As a result, additional securing of these data is possible.

In a further embodiment, data on the identification of the user and/or on the type of the at least one reaction substance and/or on the calibration for other mass flows in the case of a support gas that is different from air and/or as software update for the evaluating device are read out.

According to the current subject matter, the electronic data storage device is voided, destroyed or unreadable after the read out of the data. The voiding, destruction or rendering unreadable of the electronic data storage device is carried out, for example, by means of a pressed chip indicator pin, a color change through a moisture-sensitive layer in a capillary tube or by means of a glass rupture on the electronic data storage device, by arranging an appropriate small glass in the area of the electronic data storage device on the reaction support unit, and having this glass destroyed mechanically after the readout, so that, due to the destruction of the glass, the data from the electronic data storage device can no longer be read out, since as a result, for example, the electronic data storage device is destroyed or the reading in or out of data is no longer possible.

In a further embodiment, the gas measurement system comprises a transmission device, for example, an LED, for the emission of electromagnetic radiation, so that, with the electromagnetic radiation, it is possible to radiate through and/or onto the at least one reaction substance, and/or the gas measurement system comprises a housing, and the housing can form, in addition, the friction bearing for the reaction support unit. By means of the transmission device, the radiation is applied onto or through the reaction substance, so that as a result color changes on the reaction substance can be detected particularly precisely by the digital camera.

In an additional embodiment, the gas conveyance device is designed as a pump, particularly a suction pump, and/or the gas measurement system comprises a gas connector which can be moved between two positions, and connected fluidically to the gas conveyance device, so that, in a first position of the gas connector, no fluidic connection exists between the gas connector and the channel, and in a second position of the gas connector a fluidic connection exists between the gas connector and the channel.

The reaction support unit advantageously comprises at least two indicator pins that are movable between two positions, and one indicator pin is associated with each tube, so that, in a first position of the indicator pin, the reaction substance that has not been exposed to the gas mixture is displayable within the associated tube, and in the second position of the indicator pin, the reaction substance which has been exposed to the gas mixture is displayable within the associated tube, and/or the digital camera is arranged at a distance between 2 and 50 mm, particularly between 15 and 20 mm, from the tube, distance which is detected by the digital camera. The means for storing data contains in particular data pertaining to the reaction substance and/or the number of tubes on the reaction support unit. Depending on these stored reaction substance data for different reaction support units with different reaction substances in the tubes, the evaluation of the data acquired by the digital camera is carried out by the evaluating device.

In particular, the digital camera acquires, particularly exclusively, the colors red, green and blue, and/or the digital camera, particularly only one digital camera, detects, in the direction of flow of the gas mixture, through the channel, in a large number separate positions, for example, at least 5, 10, 50, 100 or 500 separate positions, the color change separately, and/or the digital camera detects the course over time of the color change during and/or after the conveyance of the gas mixture through the channel, and said course can be stored in an evaluation data storage device, and/or the digital camera, in particular only one digital camera, detects the color change on the reaction substance on a fictitious line in the direction of flow of the gas mixture over the entire fictitious line. The imaging optics system or the distance of the camera from the tube is configured to make it possible for the digital camera to detect the entire tube with the reaction substance, so that, in the direction of flow of the gas mixture on a fictitious line, this entire fictitious line can be detected with regard to the color change, i.e., there is no area of the reaction substance in the direction flow of the gas mixture where no determination of the color change by the digital camera occurs.

In a further embodiment, the digital camera detects the position of the reaction support unit moved by the motor, by evaluating data from an image sensor of the digital camera, particularly by means of appropriate software on the evaluating device, and the motor can be controlled depending on the position detected by the digital camera.

In an additional variant, for the fluidic connection of the gas conveyance device to the channel, a gas connector is moved to, on or in the channel, and/or before and/or during the conveyance of the gas mixture, an indicator pin associated with the channel is moved through the channel on the reaction support unit from a first position to a second position, in particular by bringing the gas connector in contact with the indicator pin during a movement of the gas connector, so that as a result the indicator pin is moved, in particular pushed, from the first position into the second position.

In a further variant, the digital camera detects the position of the indicator pin in order to detect in this manner whether no gas mixture has been passed through the channel with the reaction substance associated with the indicator pin, or that a gas mixture has already been passed through. The indicator pin here has a different color than the remaining the reaction support unit, in particular the chip or plate, and as a result it is possible for the digital camera to detect, using two corresponding different ROI (region of interest), the first and second position of the indicator pin. Based on the appropriate assignment of an indicator pin to each tube, this allows the digital camera to optically detect in a simple manner whether a gas mixture has already been passed through a tube or not. Consequently, it is possible to easily detect whether a tube has already been used for measuring the components.

In particular, the reaction support unit is introduced, for example, inserted or pushed into the remaining gas measurement system, and this is detected by the digital camera and/or the motor is controlled depending on the position detected by the digital camera, and also on the basis of the detection of the position of the indicator pin, so that the reaction support unit is moved into a position in which, if the gas connector moves, the gas connector is brought into a fluidic connection with a channel through which no gas mixture is led.

In a further interrelated aspect, an apparatus includes a housing, a friction bearing, a gas conveyance device, an optoelectronic detection device, a data reading device, an evaluating device, and a sensory feedback device. The housing defines a slot. The friction bearing is positioned within the slot and is configured to couple to a reaction support unit. The reaction support unit includes at least two light permeable channels configured to receive at least one reaction substance that changes color in presence of at least one particular gaseous or vaporous component. The gas conveyance device is configured to convey a gas mixture through at least one of the channels. The optoelectronic detection device is configured to detect a color change of the at least one reaction substance on the reaction support unit during and/or after the conveyance of the gas mixture. The color change is detected in the direction of flow of the gas mixture through the at least two channels in at least two separate positions. The data reading device is configured to read data stored on the reaction support unit and comprises at least one of a (i) a digital camera and (ii) a reading apparatus for an electronic data storage device. The evaluating device is configured to evaluate the data detected by the optoelectronic detection device. The sensor feedback device is configured to provide sensory feedback characterizing the data evaluated by the evaluating device.

In a further interrelated aspect, a method includes moving a reaction support unit through a gas measurement system, the reaction support unit having a plurality of channels each with at least one reaction substance; conveying, using a gas conveyance device, a gas mixture through a single channel of the reaction support unit; reading, by a data reading device, data from either a coding or an electronic data storage device on the reaction support unit; detecting, using a digital camera of an optoelectronic detection device, a color change of the at least one reaction substance during and/or after the conveyance of the gas mixture through the channel, wherein the color change is detected in the direction of flow of the gas mixture through the channel in at least two separate positions; evaluating, using an evaluating device, data acquired by the optoelectronic detection device with regard to the color change; and providing, using a sensory feedback device, sensory feedback regarding the evaluated data.

Advantageously, identical reaction substances for identical gaseous and/or vaporous components or different reaction substances for different gaseous and/or vaporous components are arranged in the channels. In the case of identical reaction substances on the reaction support unit, the reaction support unit can not only be used to detect identical gaseous and/or vaporous components, but the reaction support unit can also be used to detect different gaseous and/or vaporous components in the case of different reaction substances on the reaction support unit.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF THE ACCOMPANYING FIGURES

Like reference symbols in the various drawings indicate like elements.

DETAILED DESCRIPTION

Figure 4:
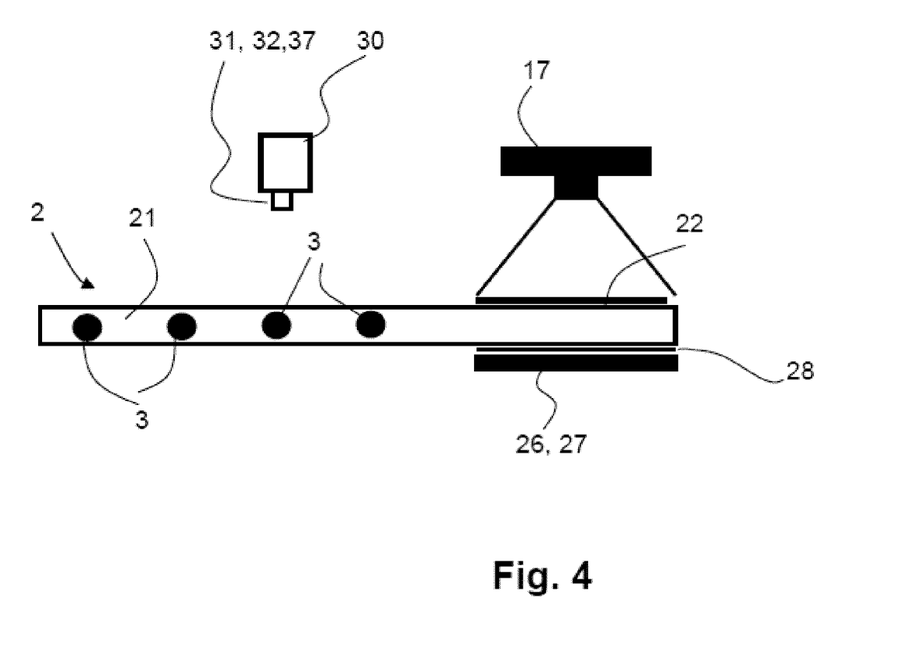
FIG. 4 shows an additional longitudinal section of the gas measurement system during a readout of the optical coding with the digital camera.
Figure 5:
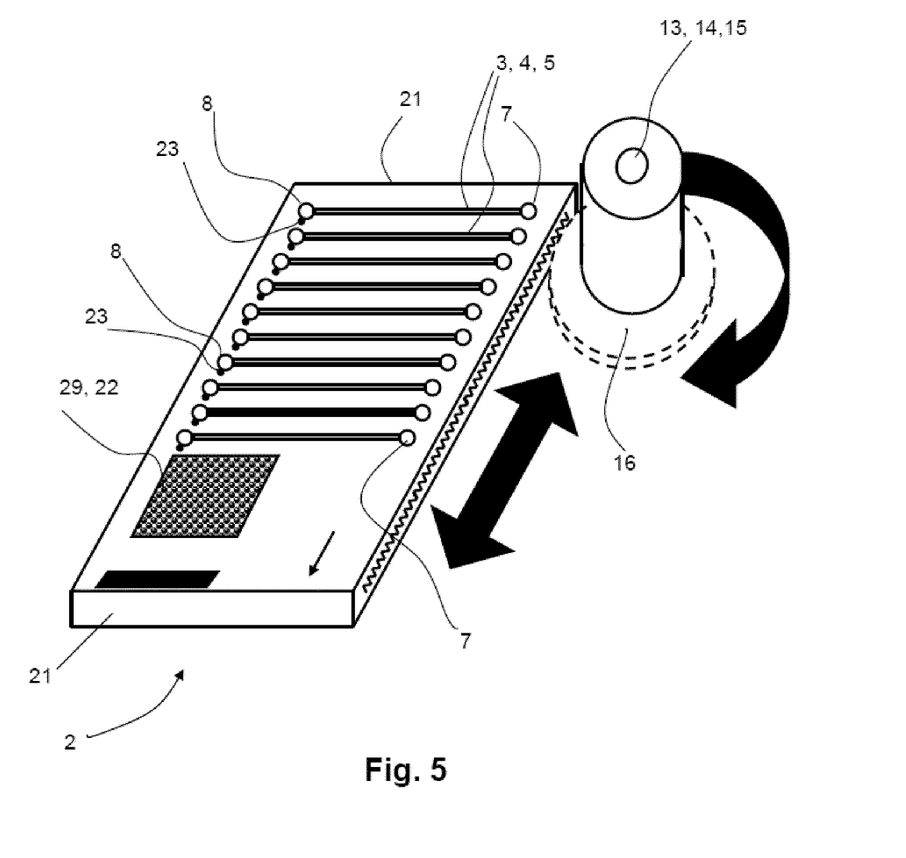
FIG. 5 shows a perspective view of the reaction support unit with a matrix coding and with a servomotor with driving roller.

A gas measurement system 1 is used for measuring or detecting the concentration of gaseous and/or vaporous components. In a gas measurement arrangement 1 or a remaining gas measurement system 1, an exchangeable reaction support unit 2 is introduced manually by hand by a user. In the process, the gas measurement system 1 is a small, portable device which can be used in a mobile manner due to its energy supply by a battery. On a housing 25 of the remaining gas measurement system 1, a pump 11 designed as a suction pump 12 is arranged, which represents a gas conveyance device 10, FIGS. 8 and 9. The housing 25 moreover forms a friction bearing for the movable reaction support unit 2. By means of a motor 13, for example, an electric motor 14 designed as a servomotor 15, and a driving roller 16 which can be set in rotation by the servomotor 15, the reaction support unit 2 can be moved within the housing 25, since a mechanical contact or a connection exists between the driving roller 16 and the reaction support unit 2, FIG. 5. Furthermore, on the remaining gas measurement system 1, a digital camera 17, LEDs 27 as transmission device 26, and color filter 28 are arranged (FIG. 4).

Figure 6:
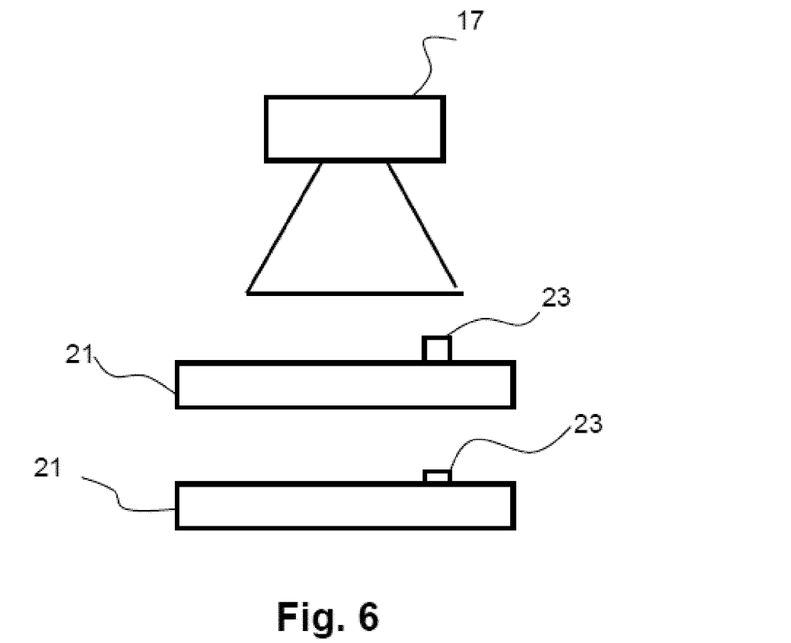
FIG. 6 shows a side view of the digital camera, of the reaction support unit with an indicator pin in a first position, and of the reaction support unit with the indicator system in a second position.
Figure 7:
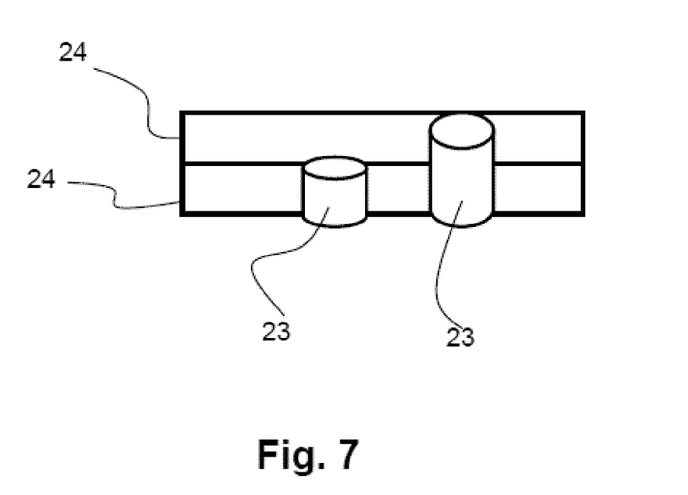
FIG. 7 shows a perspective view of the indicator system in the first position and of the indicator system in the second position.

The reaction support unit 2 comprises a chip 21 or a plate 21, which is light permeable. On a top side of the chip 21, shown in FIG. 5, ten tubes 4 designed as glass tubes 5 are arranged, so that the tubes 4 delimit a channel 3, and an identical reaction substance 6 is arranged, within this channel 3 or within the tube 4, in the ten glass tubes 5. At an end of the glass tubes 5 represented in FIG. 5 on the right, said glass tubes have an intake opening 7, and at an end of the glass tubes 5 on the left in FIG. 5, they have a discharge opening 8. The intake and discharge openings 7, 8 are here sealed in a fluid-proof manner by a seal 9, for example, a glass seal 9. As a result, it is ensured that the reaction substance 6 (FIGS. 7 and 8) within the glass tubes 5, prior to the gas mixture being passed through the tubes 4 by means of the suction pump 12, does not undergo a color change on the reaction substance 6 or the reaction substances 6, due to an unintended or uncontrollable exposure of the reaction substance to gas or vapor components. For example, the reaction substance 6 is used for detecting acetone, so that when a mixture with acetone is passed through, a color change on the reaction substance 6 occurs. In the area of the discharge openings 8, an indicator pin 23 is arranged in each case. Thus, one indicator pin 23 is associated with each one of the ten glass tubes 5, FIGS. 6 and 7, Furthermore, on the top side of the chip 21, an optical coding 22 in the form of matrix coding 23 or a matrix barcoding is also present.

Figure 8:
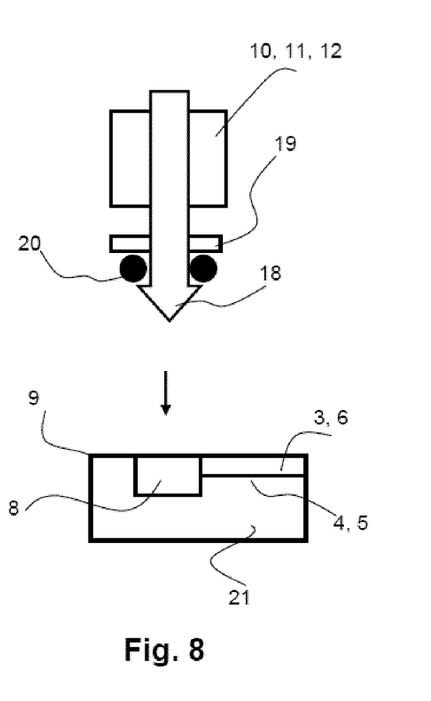
FIG. 8 shows a longitudinal section of a suction pump with gas connector in a first position and of a portion of the reaction support unit.
Figure 9:
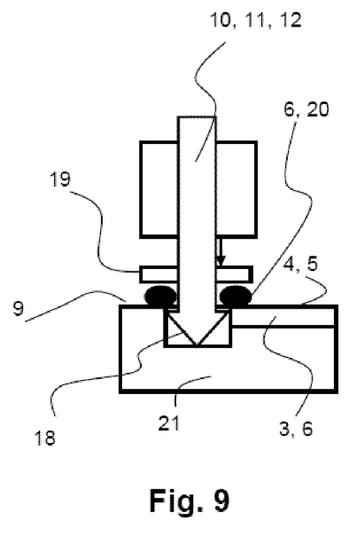
FIG. 9 shows a longitudinal section of the suction pump with gas connector in a second position and of the portion of the reaction support unit.

On the suction pump 12, a gas connector 18 is arranged, and on a support ring 19 enclosing the gas connector 18, on the bottom side, a resilient sealing ring 20, for example, a rubber or sealing ring 20, is applied to or attached to the support ring 19 (FIGS. 8 and 9). The support ring 19, in addition, has, perpendicularly to the plane of the drawing of FIGS. 8 and 9 (not shown), an enlargement in the form of an indicator pin movement element. In FIG. 8, a first position of the suction pump 12 with the gas connector 18 is represented, and in FIG. 9 a second position of the suction pump 12 with the gas connector 18 is represented. In the first position according to FIG. 8, no gas can be suctioned by the suction pump 12 through the glass tubes 5, and the seal 9 continues to be closed. During movement of the suction pump 12 with the gas connector 18, the sealing ring 9 is first broken or perforated by the gas connector 18, and subsequently the sealing ring 20 is placed outside on the top side onto the chip 21 and the glass tube 5, so that the opening inserted in the seal 9 is sealed off completely. In addition, an additional connector (not shown) perforates and opens the seal 9 on the corresponding intake opening 7 of the glass tube 5, so that the gas mixture can flow into the glass tube 5 through the intake opening 7. Subsequently, the suction pump 12 is activated, and as a result the gas mixture is suctioned in through the intake opening 7, it is subsequently led around the reaction substance 6 or the reaction substance 6 is exposed to the gas mixture, and subsequently the gas mixture is conveyed again into the surrounding environment, through the discharge opening 8, the gas connector 18, and the suction pump 12.

Figure 1:
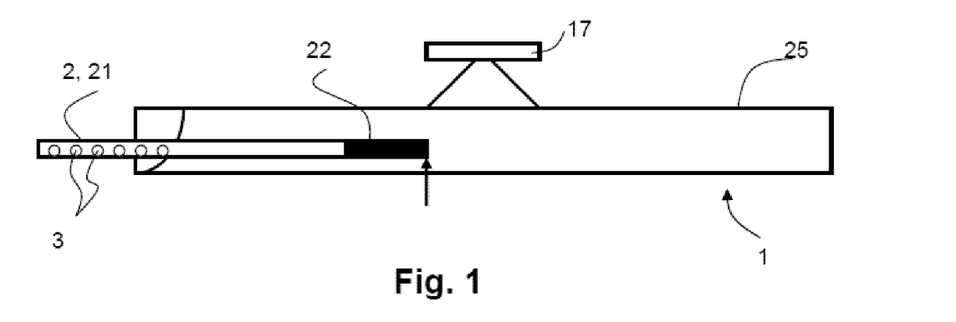
FIG. 1 shows a longitudinal section of a gas measurement system during a manual insertion of a reaction support unit into a housing.
Figure 2:
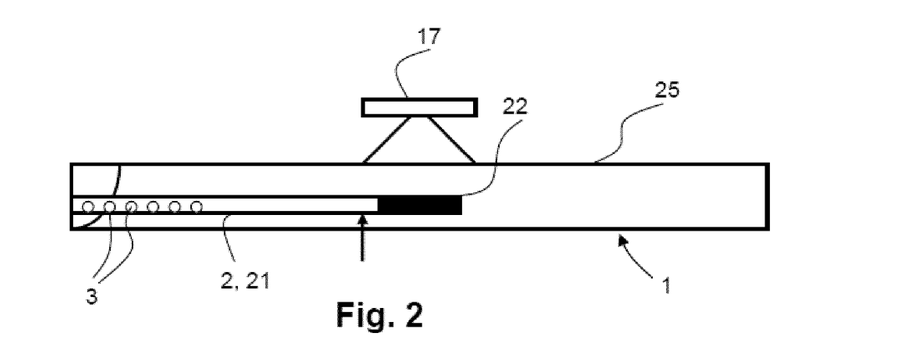
FIG. 2 shows a longitudinal section of the gas measurement system during a readout of an optical coding with a digital camera.
Figure 3:
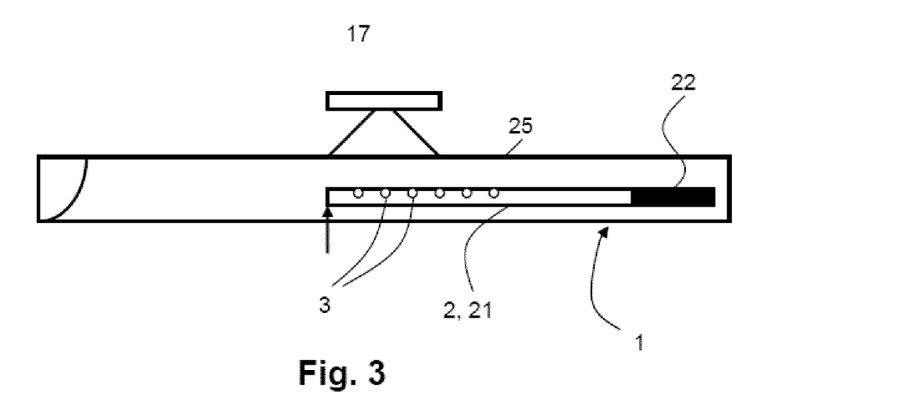
FIG. 3 shows a longitudinal section of the gas measurement system during a detection of a color change of a reaction substance with the digital camera.

For the detection of acetone using the gas measurement system 1, the reaction support unit 2 is first introduced manually into a slot on the housing 25 up to a predetermined abutment (FIG. 1). Subsequently, the servomotor 15 moves the reaction support unit 2 into the position represented in FIGS. 2 and 4. In FIGS. 1-4, for simplicity's sake, only a portion of the glass tubes 5 is represented. Here, on the remaining gas measurement system 1 on the housing 25 beneath the chip 21, the transmission device 26 with LEDs 27 and a color filter 28 are arranged. For the readout of the optical coding 22 in the form of a matrix coding 29 with the digital camera 17, the LEDs 27 are switched on, and owing to the light permeability of the chip 21, the optical coding 22 can thus be illuminated, and thus it can be read better optically by the digital camera 17. Subsequently, the servomotor 15 moves the reaction support unit 2 in a position so that the gas connector 18 is arranged above the discharge opening 8 of a first glass tube 5. The acquisition of the position of the reaction support unit 2 here also occurs simply by means of the digital camera 17, since the evaluating device has a corresponding optical software by means of which the position of the reaction support unit 2 can be detected on the basis of the data acquired by the digital camera 17. Subsequently, the suction pump 12 is moved together with the gas connector 18 downward, so that as a result the gas connector 18 perforates the seal 9, and the gas mixture can be suctioned through the discharge opening 8. In the process, an enlargement or indicator pin movement element—not shown—of the support ring 19 in addition moves the indicator pin 23, from a first position according to the upper chip 21 in FIG. 6 into a second position according to the lower chip in FIG. 6. In the first position of the indicator pin 23, the latter sticks farther out of the chip 21 than in the second position. The position of the indicator pin 23 can also be detected with the digital camera 17. The indicator pin 23 is of a different color, for example, orange, than the remaining reaction support unit 2; for example, the chip 21 is colored blue. The digital camera 17 here has two separate ROIs (region of interest) 24, so that the ROI 24 which is in the upper position in FIG. 7 in the first position in the upper ROI 24 the color orange occurs, and in the second position in the upper ROI 24 no or a substantially smaller quantity of the color of the indicator pin 23 occurs in the upper ROI 24. As a result, it is possible to detect by means of the optical evaluation software of the evaluating device whether an indicator pin 23 is in the first or second position. On the basis of this detection of the first or second position of the indicator pin 23, the reaction support unit 2 is moved furthermore in a self actuating manner and automatically by the servomotor 15 in a position such that the first, so far unused, glass tube 4, through which so far no gas mixture has been led, is located with the discharge opening 8 above the gas connector 18, and it is only subsequently that the suction pump 12 and the gas connector 18 are moved downward.

After passing the gas mixture through the glass tube 5, if the concentration of acetone as gaseous and/or vaporous component is sufficient, a color change occurs on the reaction substance 6 within the glass tube 5. This color change is detected by the digital camera 17 in a large number of separate positions, for example, 30 different positions, as a function of time. Due to the large pixel number of the digital camera 17 and the evaluation of the data supplied by the digital camera 17, this can be done simply by the optical evaluation software in the evaluating device. These data supplied by the digital camera 17 are stored in an evaluation data storage device, and it is only after the completion of the color change and the complete passage of the gas mixture through the glass tube, that an evaluation of the data acquired by the digital camera 17 is carried out, with a view to determining the color change on the reaction substance 6. If a predetermined concentration of acetone is exceeded, a warning signal is issued by a indicator device which is not shown.

During the detection of the color change of the reaction substance 6 with the digital camera 17, the display device 26 is switched on furthermore, and, due to the color filter 28, only electromagnetic radiation within a predetermined frequency range reaches the reaction substance 6, because the chip 21 is light permeable and the glass tube 5 is transparent. As a result, illumination of the reaction substance 6 occurs during the color change and the detection with the digital camera 17, resulting in a more precise and better determination of the color change by means of the digital camera 17.

In a further embodiment example—not shown—of the gas measurement system 1, different reaction substances for different gaseous and/or vaporous components are arranged in each of the ten glass tubes 5. After inserting the reaction support unit 2 and after reading the matrix coding 29, on which this is stored appropriately, namely that different reaction substances are arranged in the glass tube 5, then one after the other, independently, all ten glass tubes 5 are exposed to the passage of a gas mixture through them by the suction pump 12, analogously to the above-explained embodiment example, and the color change is detected by the digital camera 17. As a result, in this embodiment example, ten different gaseous and/or vaporous components can be detected by the gas measurement system 1.

Figure 10:
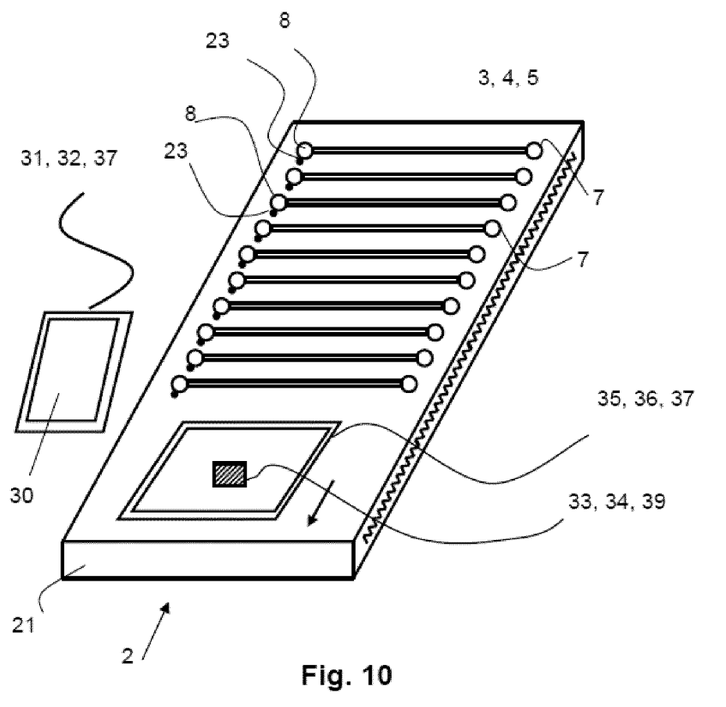
FIG. 10 shows a perspective view of the reaction support unit with a RFID chip.

FIG. 10 is a representation of a second embodiment example of the reaction support unit 2. On the reaction support unit 2, on the top side, on the plate 21, a RFID chip 34 is arranged as an electronic data storage device 33 or a means for storing data. Furthermore, in the area of the RFID chip 34, a transmitter 35 and a receiver 36 of the RFID chip 34 are arranged, which are designed as antenna 37. This antenna 37 can also be integrated in the RFID chip 34. On the gas measurement system 1, particularly on a housing of the gas measurement system 1, a reading apparatus 30 (FIG. 4) with a transmitter 31 and a receiver 32 on the reading apparatus 30, is arranged. The transmitter 31 and the receiver 32 on the reading apparatus 30 are antennas 37 here as well. As a result, the data stored in the RFID chip 34 can be transferred by means of the transmitter 35 from the RFID chip 34 to the receiver 32 on the reading apparatus 30 by means of a radio connection. The RFID chip 34 can here be designed as an active RFID chip with its own energy supply or also as a passive RFID chip without its own energy supply. The data transfer here occurs thus by means of an alternating electromagnetic field, and, in the case of a passive RFID chip, the energy supply for the RFID chip also occurs by means of the alternating electromagnetic field. In the process, data can also be transferred from the reading apparatus 30 to the RFID chip 34, since the antenna 37 on the reading apparatus 30 also functions as a transmitter 31, and the antenna 37 on the RFID chip also functions as a receiver 36. The data read out by the reading apparatus 30 on the RFID chip can subsequently be transferred to the evaluating device of the gas measurement system 1.

Figure 11:
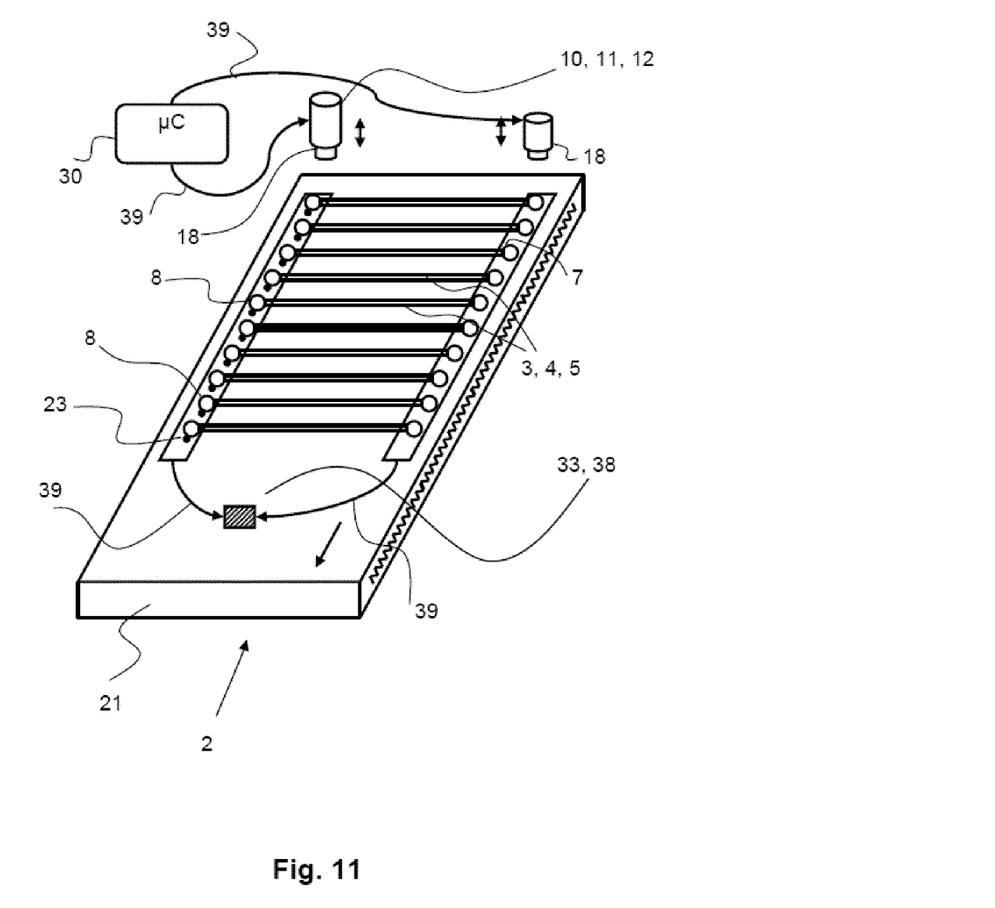
FIG. 11 shows a perspective view of the reaction support unit with a RAM chip.

In FIG. 11, a third embodiment example of the reaction support unit 2 with an SRAM chip 38 as electronic data storage device 33 is represented. On the top side, on the plate 21, the SRAM chip 38 is arranged and by means of two data lines 39 a current-conducting connection is established for the intake and discharge openings 7, 8 on the tube 4. For the passage of gas through the tube 4, the gas connectors 18 have to be moved to the intake and discharge openings 7, 8. Here, the gas connectors 18 are produced from a current-conducting material, for example, a metal, and they are connected by means of an additional data line 39 to a reading apparatus 30 on the housing of the gas measurement system 1 in a current and data conducting manner. As a result, a current or data connection can be established between the SRAM chip 38 and the reading apparatus 30, while the gas connectors 18 are located in the intake and discharge openings 7, 8. The time available for this purpose is sufficient to be able to transmit all the data stored in the SRAM chip 38 onto the reading apparatus 30. In the process, data can also be transferred from the reading apparatus 30 to the SRAM chip 38. The data stored in the reading apparatus 30 after the readout are subsequently transferred to the evaluating device.

When using electronic data storage devices 33, data can also be stored in the electronic data storage devices 33 before the reaction support unit 2 has been inserted into the remaining gas measurement system 1 for a measurement. As a result, prior to a measurement or a determination of the concentration of the gaseous and/or vaporous components, limit values or additional usage-specific/data are stored on the electronic data storage device 33 by a user, and said data are then transferred, after the insertion of the reaction support unit 2 into the remaining gas measurement system 1, to the evaluating device, and taken into consideration during the evaluation. For this purpose, a data connection has to be established only between the electronic data storage device 33 and an input device, for example, a computer, particularly a laptop computer. Here, the data stored in the electronic data storage device 33 are configured so that a specific format is present, and consequently so that a manipulation of the data is in general not possible. In addition, data pertaining to the authorization or the identity of a user of the gas measurement system 1 can also be stored on the electronic data storage device 33. As a result, certain user groups, for example, user, admin., guest, can be defined, so that for differing uses of the gas measurement system 1, the different user groups receive differing rights for the use of the gas measurement system 1. In addition, in the electronic data storage device 33, settings regarding limit values for releases, warnings and approval as well as software can be stored as updates.

In the matrix coding 29 or on the electronic data storage device 33, larger data quantities can be stored and read, securely and reliably. This opens new possibilities for increasing the precision in the detection of the concentration of gaseous and/or vaporous components of the gas mixture. In particular, during a detection of the color change of the at least one reaction substance 6 by means of a digital camera 17, a large number of different color change positions can be detected by the digital camera 17, so that here too larger data quantities are generated, and correspondingly larger data quantities can also be made available to the evaluating device for the purpose of an exact evaluation.

In a particular embodiment example, a gas measurement system 1 for measuring the concentration of gaseous and/or vaporous components of a gas mixture by means of a color change of at least one reaction substance 6 on a reaction support unit 2 is provided, wherein the at least one reaction substance 6 on the reaction support unit 2 is arranged separately within at least two light permeable channels 3. Therein, the gas measurement system 1 comprises a gas conveyance device 10 for conveying the gas mixture through a channel 3 and to the at least one reaction substance 6; a mechanical bearing, in particular a friction bearing, for the reaction support unit 2; preferably a motor 13 for moving the reaction support unit 2 or another component, so that the gas mixture can be conveyed separately through one of the at least two channels 3; an optoelectronic detection device for detecting a color change of the at least one reaction substance 6 during and/or after the conveyance of the gas mixture through a channel 3, wherein the color change can be detected preferably in the direction of flow of the gas mixture through the channel 3 in at least two separate positions; a data reading device for the readout of data stored on the reaction support unit; an evaluating device for evaluating the data detected by the optoelectronic detection device; an optical and/or acoustic display device for displaying the data evaluated by the evaluating device. Therein, the data reading device can be designed as a digital camera 17 and/or as a reading apparatus 30 for an electronic data storage device 33. In such a gas measurement system, the reading apparatus 30 can comprise a receiver 32, for example, an antenna 37, and preferably a transmitter 31, for example, an antenna 37, for wireless signals, for example, alternating magnetic fields or radio waves. Further, said reading apparatus 30 can comprise electrical contact elements for hard-wired data transfer from the reaction support unit 2 to the gas measurement system 1, and preferably vice versa. Also, said reading apparatus 30 can comprise a bus system or a portion of a bus system for hard-wired data transfer from the reaction support unit 2 to the gas measurement system 1, and preferably vice versa. In said gas measurement system, the reading apparatus 30 can be formed at least partially, particularly completely, by the evaluating device. Also, the digital camera 17 can be designed with an electronic image converter or image sensor and with an imaging optics system, preferably a lens system, and/or the digital camera 17 can be designed as a camera chip, particularly a CMOS camera chip, and/or the optoelectronic detection device can be formed by the digital camera 17. In said gas measurement system, the motor 13 can be designed as an electric motor 14, particularly a servomotor 15, and the motor 13 can preferably be moved by means of a driving roller 16 into an effective mechanical connection with the reaction support unit 2, and/or the evaluating device can comprise a processor, for example, a microcontroller, and an evaluation data storage device, and/or the display device can comprise a monitor and/or a light emitter, for example, a lamp or an LED and/or a signal tone generator, and/or a method as described subsequently can be carried out with a gas measurement system 1, and/or the gas measurement system 1 can comprise the subsequently described reaction support unit 2.

Such a reaction support unit 2, particularly a reaction support unit 2 for the described gas measurement system 1, can comprise a chip 21 or a plate 21 and—arranged on the chip 21 or the plate 21—tubes 4, particularly glass tubes 5, which delimit the channels 3, and—within the tubes 4—at least one reaction substance 6 can be arranged, and a means for storing data, wherein the means for storing data can be designed as a matrix coding 29, particularly a matrix barcode, or as an electronic data storage device 33. Therein, the electronic data storage device 33 can be designed as a RFID chip 34 as a RAM data storage device, particularly an SRAM chip or an NVRAM chip, or as a ROM data storage device, particularly a PROM chip or an EPROM chip, and/or the reaction support unit 2 can comprise a transmitter 35, for example, an antenna 37, and preferably a receiver 36, for example, an antenna 37, for wireless signals, for example, for magnetic alternating fields or radio waves, and/or the reaction support unit 2 can comprise electrical contact elements and/or a bus system or a portion of a bus system for hard-wired data transfer from the reaction support unit 2 to the gas measurement system 1, and preferably vice versa. Further, in said reaction support unit 2 the matrix coding 29 can be designed as a printed matrix coding, printed in particular on the chip or the plate, or the matrix coding 29 can be designed as an LED arrangement.

Additionally, a method for operating a gas measurement system 1—namely for operating the gas measurement system 1 as described above—can comprise the steps: preferably moving a reaction support unit 2 or another component with a motor 13; transferring data from a means for storing data in the reaction support unit 2 by means of a data reading device to the gas measurement system 1, in particular to a display device of the gas measurement system 1; conveying a gas mixture through a, in particular only one, channel 3 with at least one reaction substance 6 by means of a gas conveyance device 10; detecting a color change by means of an optoelectronic detection device for detecting the at least one reaction substance 6 during and/or after the conveyance of the gas mixture through the channel 3, wherein the color change is detected preferably in the direction of flow of the gas mixture through the channel 3 in at least two separate positions; evaluating the data acquired by the optoelectronic detection device with regard to the color change by means of an evaluating device; optical and/or acoustic display of the data evaluated by the evaluating device by means of a display device, wherein the data are read out from a matrix code 29 or an electronic data storage device 33. In this a method, the data can be read out optically using a digital camera 17 or by a hard-wired or wireless process, particularly by means of radio waves or a modifiable magnetic field, with a reading device 30. Further, data pertaining, for example, to the concentration of gaseous and/or vaporous components of the gas mixture can be transferred to the electronic data storage device 33, in particular from the evaluating device, in particular by means of the reading apparatus 30, and/or the color change of the at least one reaction substance 6 is detected, in particular exclusively, with a digital camera 17. Also, the data can be read out on the identification of the user and/or on the type of the at least one reaction substance 6 and/or on the calibration for other mass flows in the case of a support gas that is different from air and/or as software update for the evaluating device. Finally, the electronic data storage device 33 can be voided, destroyed or rendered unreadable after the readout of the data.

LIST OF REFERENCE NUMERALS

1 Gas measurement system
2 Reaction support unit
3 Channel
4 Tube
5 Glass tube
6 Reaction substance
7 Intake opening on glass tube
8 Discharge opening on glass tube
9 Seal
10 Gas conveyance device
11 Pump
12 Suction pump
13 Motor
14 Electric motor
15 Servomotor
16 Driving roller
17 Digital camera
18 Gas connector
19 Support ring on gas connector
20 Sealing ring
21 Chip, plate
22 Optical coding
23 Indicator pin
24 ROI
25 Housing
26 Transmission device 27 LED
28 Color filter
29 Matrix coding
30 Reading apparatus
31 Transmitter on the reading apparatus
32 Receiver on the reading apparatus
33 Electronic data storage device
34 RFID chip
35 Transmitter on the RFID chip
36 Receiver on the RFD chip
37 Antenna
38 SRAM chip
39 Data line One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

The invention claimed is:

1. An apparatus comprising:
   a housing defining a slot;
   a reaction support unit;
   a friction bearing within the slot configured to couple to the reaction support unit, the reaction support unit comprising at least two light permeable channels configured to receive at least one reaction substance, the at least one reaction substance changing color in presence of at least one particular gaseous or vaporous component;
   a gas conveyance device configured to convey a gas mixture through at least one of the channels;
   an optoelectronic detection device configured to detect a color change of the at least one reaction substance on the reaction support unit during and/or after the conveyance of the gas mixture, the color change being detected in the direction of flow of the gas mixture through the at least two channels in at least two separate positions;
   a data reading device configured to read data stored on the reaction support unit, the data reading device comprising a digital camera;
   an evaluating device configured to evaluate the data detected by the optoelectronic detection device; and
   a sensory feedback device configured to provide sensory feedback characterizing the data evaluated by the evaluating device.

2. An apparatus as in claim 1, wherein the digital camera comprises and imaging optics system and at least one of (i) an electronic image converter and (ii) image sensor.

3. An apparatus as in claim 2, wherein the imaging optics system comprises a lens system.

4. An apparatus as in claim 1, wherein the digital camera comprises a camera chip.

5. An apparatus as in claim 4, wherein the camera chip is a CMOS camera chip.

6. An apparatus as in claim 1, wherein the data reading device comprises the digital camera and the optoelectronic detection device is formed by the digital camera.

7. An apparatus as in claim 1, wherein the friction bearing comprises a motor that is configured to be moved, via a driving roller, into an effective mechanical connection with the reaction support unit.

8. An apparatus as in claim 7, wherein the motor is an electric motor.

9. An apparatus as in claim 8, wherein the electric motor is a servomotor.

10. An apparatus as in claim 1, wherein the evaluating device comprises a processor and an evaluation data storage device.

11. An apparatus as in claim 1, wherein the sensory feedback device comprises at least one device selected from a group consisting of: a monitor, a light emitter, a lamp, an LED, and a signal tone generator.

12. An apparatus as in claim 1, the digital camera is located at a position above the reaction support unit.

13. An apparatus as in claim 12, wherein the reaction support unit comprises a supporting surface with a plurality of tubes disposed therein that delimit the channels, and wherein the at least one reaction substance is arranged within the tubes.

14. An apparatus as in claim 13, wherein the supporting surface comprises a chip or a plate.

15. An apparatus as in claim 13, wherein the tubes comprise glass tubes.

16. An apparatus as in claim 12, wherein the reaction support unit further comprises an optical coding.

17. An apparatus as in claim 16, wherein the coding is selected from a group consisting of: a bar code, a matrix coding, and an RFID chip.

18. An apparatus an in claim 16, wherein the coding is a matrix coding comprises a printed matrix coding or as an LED arrangement.

19. An apparatus as in claim 12, wherein the reaction support further comprises an electronic data storage device.

20. An apparatus as in claim 19, wherein the electronic data storage device is one of: an RFID chip, a RAM data storage device, an SRAM chip, an NVRAM chip, a ROM data storage, a PROM chip, and an EPROM chip.

21. An apparatus as in claim 12, wherein the reaction support unit comprises a transmitter and a receiver.

22. An apparatus as in claim 21, wherein the transmitter comprises an antenna and the receiver comprises an antenna.

23. An apparatus as in claim 22, wherein the antennas transmit and receive magnetic alternating fields or radio waves.

24. An apparatus as in claim 12, wherein the reaction support unit comprises electrical contact elements and/or at least a portion of a bus system for hard-wired data transfer to and/or from the reaction support unit.

25. An apparatus as in claim 1, further comprising:
a pump movable between at least a first position and a second position, each of the at least two light permeable channels having a sealed inlet and a sealed outlet, the pump being located at a spaced location from each of the at least two light permeable channels in the first position, wherein a portion of the pump penetrates the sealed outlet in the second position.

26. An apparatus as in claim 25, wherein the pump is perpendicular to the reaction support unit.

27. An apparatus as in claim 25, wherein the pump is located at a position above the reaction support unit in the first position.

28. An apparatus comprising:
a housing defining a slot;
a reaction support unit
a friction bearing within the slot configured to couple to the reaction support unit, the reaction support unit comprising at least two light permeable channels configured to receive at least one reaction substance, the at least one reaction substance changing color in presence of at least one particular gaseous or vaporous component;
a gas conveyance device configured to convey a gas mixture through at least one of the channels;
an optoelectronic detection device comprising a digital camera configured to detect a color change of the at least one reaction substance on the reaction support unit during and/or after the conveyance of the gas mixture, the color change being detected in the direction of flow of the gas mixture through the at least two channels in at least two separate positions;
a data reading device configured to read data stored on the reaction support unit;
an evaluating device configured to evaluate the data detected by the optoelectronic detection device; and
a sensory feedback device configured to provide sensory feedback characterizing the data evaluated by the evaluating device.

29. An apparatus as in claim 28, further comprising:
a pump movable between at least a first position and a second position, each of the at least two light permeable channels having a sealed inlet and a sealed outlet, the pump being located at a spaced location from each of the at least two light permeable channels in the first position, wherein a portion of the pump penetrates the sealed outlet of one of the at least two light permeable channels in the second position.

30. An apparatus as in claim 29, wherein the pump is perpendicular to the reaction support unit.

31. An apparatus as in claim 29, wherein the pump is located at a position above the reaction support unit in the first position.

32. An apparatus as in claim 28, wherein the digital camera is located at a position above the reaction support unit.

33. An apparatus comprising:
a housing defining a slot;
a friction bearing within the slot configured to couple to a reaction support unit, the reaction support unit comprising at least two light permeable channels configured to receive at least one reaction substance, the at least one reaction substance changing color in presence of at least one particular gaseous or vaporous component;
a gas conveyance device configured to convey a gas mixture through at least one of the channels;
an optoelectronic detection device comprising a digital camera configured to detect a color change of the at least one reaction substance on the reaction support unit during and/or after the conveyance of the gas mixture, the color change being detected in the direction of flow of the gas mixture through the at least two channels in at least two separate positions, the digital camera being further configured to read data stored on the reaction support unit;
an evaluating device configured to evaluate the data detected by the optoelectronic detection device; and
a sensory feedback device configured to provide sensory feedback characterizing the data evaluated by the evaluating device.

34. An apparatus as in claim 33, further comprising:
a pump movable between at least a first position and a second position, each of the at least two light permeable channels having a sealed inlet and a sealed outlet, the pump being located at a spaced location from each of the at least two light permeable channels in the first position, wherein a portion of the pump penetrates the sealed outlet of one of the at least two light permeable channels in the second position.

35. An apparatus as in claim 34, wherein the pump is perpendicular to the reaction support unit.

36. An apparatus as in claim 34, wherein the pump is located at a position above the reaction support unit in the first position.

37. An apparatus as in claim 33, wherein the digital camera is located at a position above the reaction support unit.

* * * * *